United States Patent [19]

Boxler et al.

[11] 4,391,823

[45] Jul. 5, 1983

[54] NOVEL POLYCYCLIC INSECTICIDAL ESTERS

[75] Inventors: Dena L. Boxler, Lockport, N.Y.; Albert C. Chen, East Brunswick, N.J.

[73] Assignee: Rhone-Poulenc Agrochimie, Lyons, France

[21] Appl. No.: 285,241

[22] Filed: Jul. 20, 1981

Related U.S. Application Data

[63] Continuation-in-part of Ser. No. 122,228, Feb. 19, 1980, abandoned.

[51] Int. Cl.³ .................. C07C 69/743; C07C 69/747; C07C 69/612; A01N 53/00
[52] U.S. Cl. ................................. 424/306; 424/304; 424/305; 424/308; 560/9; 560/55; 560/105; 560/124; 260/464; 260/465 D
[58] Field of Search .................. 560/124, 9, 55, 105; 260/465 D; 424/304, 305, 306, 308

[56] References Cited

U.S. PATENT DOCUMENTS

3,679,667 7/1972 Fanta ................................. 560/124
4,197,408 4/1980 Arantani ........................... 560/124

FOREIGN PATENT DOCUMENTS

46-6918 2/1971 Japan ................................. 560/124
46-41633 12/1971 Japan ................................. 560/124

OTHER PUBLICATIONS

Sugawara, Agric. Biol. Chem. 42, pp. 847–850 (1978).

*Primary Examiner*—Michael L. Shippen
*Attorney, Agent, or Firm*—Burns, Doane, Swecker & Mathis

[57] ABSTRACT

Dimethyl dichlorovinylcyclopropyl carboxylic acid esters of substituted (alkyl, aryl, halo, amino, etc.) polycyclic alcohols are insecticidal.

45 Claims, No Drawings

NOVEL POLYCYCLIC INSECTICIDAL ESTERS

CROSS REFERENCE TO RELATED APPLICATIONS

This application is a Continuation-in-Part of copending U.S. application Ser. No. 122,228, filed Feb. 19, 1980, now abandoned.

BACKGROUND OF THE INVENTION

1. Field of the Invention

This invention is concerned with insecticidal esters of polycyclic alcohols.

2. Description of the Prior Art

Certain insecticidal esters have been described in U.S. Pat. Nos. 4,024,168 and 4,062,968. Insofar as is now known, the esters of this invention have not been proposed.

SUMMARY OF THE INVENTION

This invention provides insecticidal compounds having the formula:

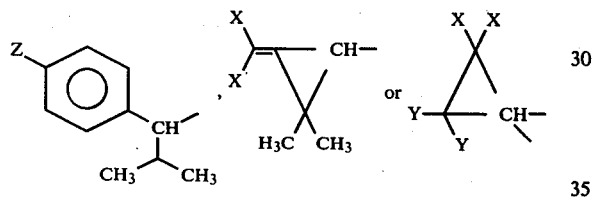

wherein X is F, Cl, Br, or methyl; Y is methyl or Cl; Z is F, Cl, Br, $CF_3$, $CF_3O$, $CF_3S$, $CHF_2$, $CHF_2O$, or $CHF_2S$;

$R^2$ is

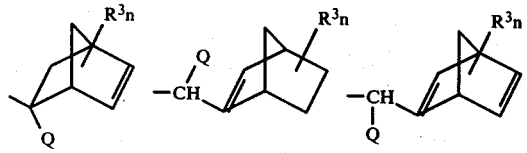

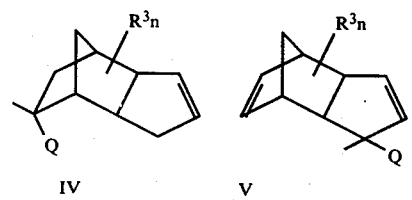

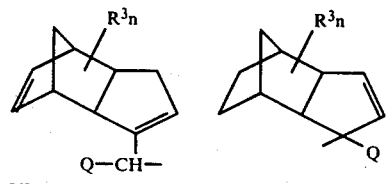

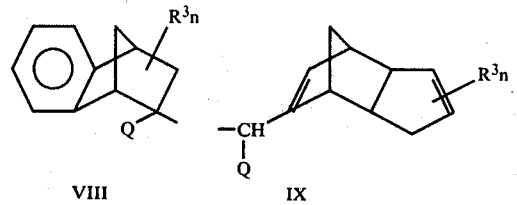

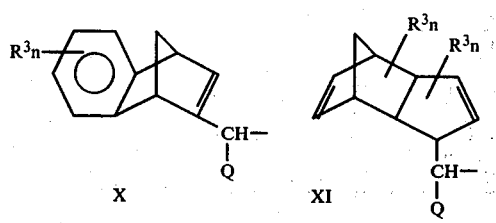

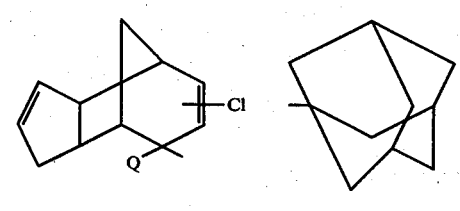

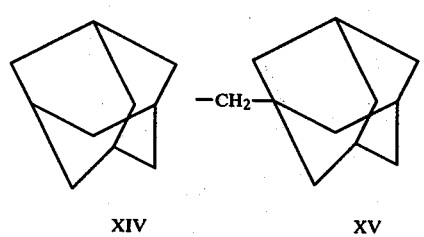

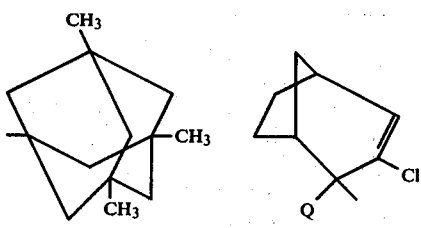

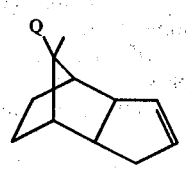

wherein $R^3$ is the same or different hydrogen, alkyl, aryl, substituted aryl, $C_2$-$C_4$ alkenyl, $C_2$-$C_4$ alkynyl, alkoxy, amino, alkylamino, dialkylamino, halo (F, Cl, Br), haloalkyl, alkylthio, alkylsulfonyl, alkoxyalkyl, cyano or nitro in which alkyl and alkoxy are $C_1$-$C_4$; Q is H, CN or —C≡CH; and n is 1-8.

DESCRIPTION OF SPECIFIC EMBODIMENTS

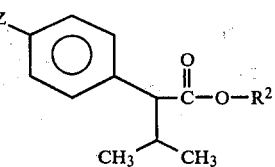

| Z | R² | Q | R³ | n |
|---|---|---|---|---|
| F | I | H | CH₃ | 1 |
| CF₃ | I | CN | CH₃ | 1 |
| CF₃O | IV | CH≡C | H | 1 |
| CF₃S | XI | CN | C₂H₅ | 1 |
| CHF₂ | VI | H | Cl | 2 |
| CHF₂O | VIII | H | H | 1 |
| Br | XIV | H | CN | 1 |

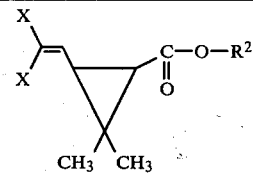

| X | R² | Q | R³ | n |
|---|---|---|---|---|
| F | I | H | CH₃ | 1 |
| Br | IV | CN | H | 1 |
| Cl | XI | H | C₂H₅ | 1 |
| CH₃ | VII | CH≡C | H | 1 |
| Br | X | H | CH₃ | 1 |
| F | XIII | H | Cl | 3 |
| Cl | II | CN | H | 1 |

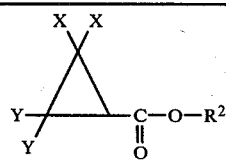

| X | Y | R² | Q | R³ | n |
|---|---|---|---|---|---|
| CH₃ | CH₃ | III | H | H | 1 |
| F | CH₃ | VIII | H | C₂H₅ | 1 |
| Cl | Cl | XI | CN | H | 1 |
| CH₃ | Cl | VII | CH≡C | H | 1 |
| Br | CH₃ | I | H | H | 1 |
| F | CH₃ | XII | CN | Cl | 1 |
| CH₃ | CH₃ | IV | H | CH₃ | 1 |

The esters of this invention can be prepared by any of the well known techniques of esterification. For example, the carboxylic acid reactant can be esterified with the alcohol reactant, preferably using an azeotroping solvent (benzene, xylene, toluene) to remove water of esterification. Also, vacuum techniques can be employed to remove the water.

Another technique is to react a halide of the carboxylic acid reactant with the alcohol reactant, employing a tertiary amine hydrogen halide acceptor.

The carboxylic acid reactants are known in the art, e.g., in U.S. Pat. Nos. 4,024,163 and 4,062,968 which are incorporated herein by reference. The alcohols also are known, but have not been proposed in insecticides of the present type.

The following information shows typical availability either through commercial sources or through synthesis methods known to those skilled in the art of polycyclic alcohol derivatives cited as the R² substituent in the general formula. In all examples, Q is hydrogen and the Roman numerals refer to the structures set forth on page 2.

III

This structure is prepared by a Diels-Alder reaction between cyclopentadiene (commercially available as the dimer) and propargyl alcohol at about 130° C.

V

This alcohol can be prepared allylic oxidation of cyclopentadiene dimer with SeO₂.

VIII

This alcohol is prepared by a Diels-Alder reaction of cyclopentadiene dimer with benzyne followed by reaction with diborane and then with hydrogen peroxide and base (source of OH⁻).

XI

The synthesis of this alcohol starts with the alcohol of structure V, supra. It is oxidized, using any of a variety of reagents, such as Jones Reagent, to form the corresponding ketone. This is then reacted with the triphenyl phosphonium compound Q₃P=CH—OC₂H₅ to form the compound of the structure:

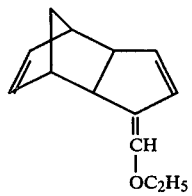

This compound is then hydrolyzed in the presence of protic acid to form the aldehyde, which is converted to the alcohol XI with sodium tetrahydroborate.

Typical examples of the preparation of compounds of this invention are as follows:

EXAMPLE 1

A solution of 2,2-dimethyl-3-dichlorovinyl cyclopropyl acid chloride (3.2 g., 0.014 mol) in dry toluene (50 ml) was added dropwise to a solution of 2-hydroxymethyl-5-norbornene (1.7 g., 0.014 mol) and dry pyridine (2.3 ml, 0.028 mol) in dry toluene (50 ml). After 16 hrs. at room temperature, the reaction mixture was poured into water and the layers separated. The aqueous layer was extracted twice with ether. The combined organic fractions were washed with water, sat. NaCl solution, dried over MgSo₄ and concentrated under reduced pressure. The residue was chromatographed on silica gel with 10% methylene chloride in hexane to separate cis and trans isomers. The total yield was 3.0 g clear oil (68%). Upon standing the trans isomer solidified (m.p. 50°-53°).

1-trans NMRδ (relative to TMS): 5.72 (d, 1H, J=8), 5.93–6.47 (m, 2H), 4.83 (dd, 2H), 1.30 (S, 3H), 1.20 (S, (S, 3H).

EXAMPLE 7

A suspension of 2,2-dimethyl-3-dichlorovinyl cyclopropyl acid chloride (4.2 g., 0.02 mol), 3,4-dichlorobicyclo-[3.2.1]-oct-2-ene (1.8 g., 0.01 mol) and anhydrous potassium carbonate (3.4 g., 0.024 mol) in 2-butanone (100 ml) was refluxed for 3 days. After cooling, the reaction mixture was filtered and the filtrate concentrated under reduced pressure. The residue was dissolved in 10% methylene chloride in hexane and refiltered. The filtrate was evaporated and the residue chromatographed on silica gel with 10% methylene chloride in hexane to separate cis and trans isomers. The total yield was 1.4 g (40%) of a clear oil. 7-cis NMRδ (relative to TMS): 6.28 (d, 2H, J=7), 4.92–5.10 (M, 1H), 1.23 (S, 6H).

In a similar manner other compounds having the following structures were prepared:

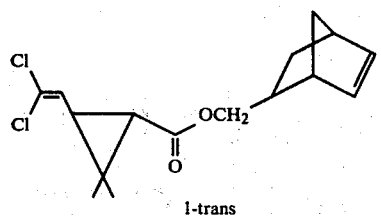

1-trans

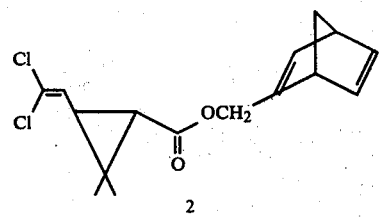

2

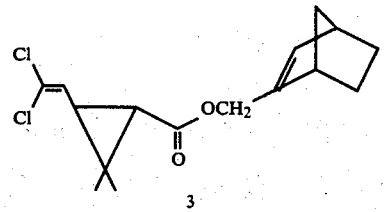

3

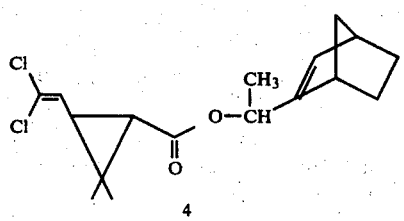

4

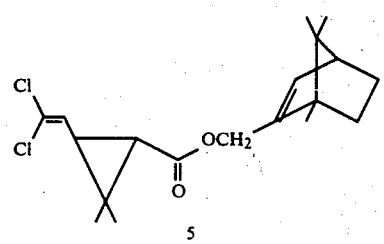

5

-continued

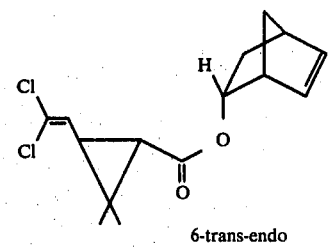

6-trans-endo

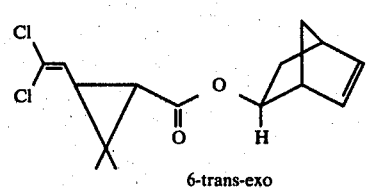

6-trans-exo

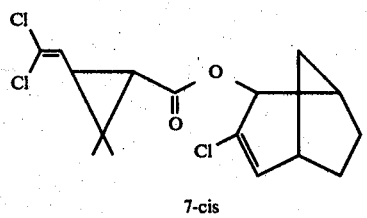

7-cis

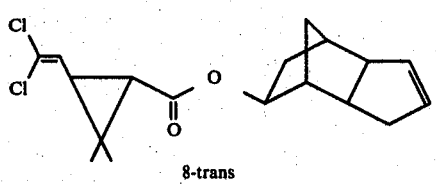

8-trans

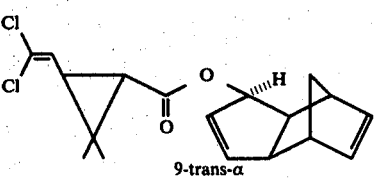

9-trans-α

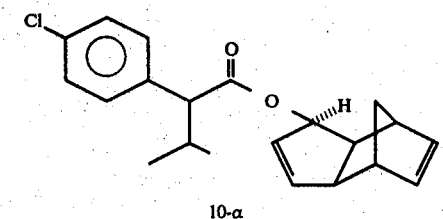

10-α

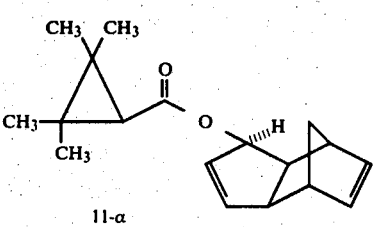

11-α

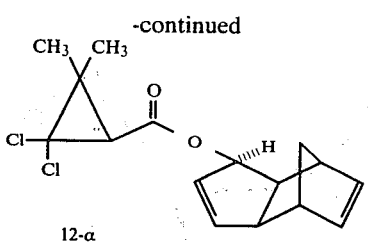

12-α

13-trans-β

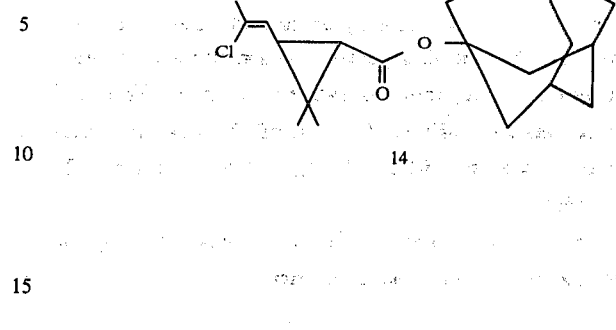

14

Starting materials and NMR data, other than for Examples 1 and 7 are set forth in Table I.

TABLE I

| Example | Acid Chloride | Alcohol | Yield | NMRδ (relative to TMS) |
|---|---|---|---|---|
| 2 | 2,2-dimethyl-3-dichlorovinyl cyclopropyl acid chloride | 2-hydroxymethyl bicyclo-[2.2.1]-2,5-heptadiene | — | |
| 3 | 2,2-dimethyl-3-dichlorovinyl cyclopropyl acid chloride | 2-hydroxymethyl bicyclo-[2.2.1]-hept-2-ene | 42% | [6.30 (d, J = 8, cis), 5.65 (d, J = 8, trans) 1H], 5.83–6.00 (M, 1H), 4.66 (bs, 2H), [1.27 (S, trans), 1.21 (s, cis), 1.16 (S,trans) 6H] |
| 4 | 2,2-dimethyl-3-dichlorovinyl cyclopropyl acid chloride | 2-(1-hydroxyethyl)$^{(a)}$ bicyclo-[2.2.1]-hept-2-ene | 64% | |
| 5 | 2,2-dimethyl-3-dichlorovinyl cyclopropyl acid chloride | 2-hydroxymethyl$^{(b)}$ 1,7,7-trimethyl bicyclo-[2.2.1]-hept-2-ene | 45% | [6.40 (d, J = 8, cis), 5.73 (d, J = 8, trans) 1H], 5.93–6.10 (M, 1H) 4.68 (bs, 2H), [1.29 (S, trans), 1.24 (S, cis), 1.20 (S, trans) 6H], 1.01 (S, 3H), 0.79 (S, 6H) |
| 6 | 2,2-dimethyl-3-dichlorovinyl cyclopropyl acid chloride | 5-norbornene-2-ol | 54% | 6-trans-endo: 5.90–6.50 (M, 2H), 5.63 (d, 1H, J = 8), 5.12–5.48 (M, 1H), 3.0–3.3 (M, 1H), 2.73–3.0 (M, 1H), 1.23 (S, 3H), 1.12 (S, 3H) 6-trans-exo: 5.93–6.50 (M, 2H), 5.70 (d, 1H, J = 8), 4.57–4.87 (M, 1H) 2.70–3.0 (M, 2H), 1.27 (S, 3H), 1.15 (S, 3H) |
| 8-trans | 2,2-dimethyl-3-dichlorovinyl cyclopropyl acid chloride | 8-hydroxy-tricyclo-[5.2.1.0$^{2.6}$] dec-3-ene | — | 5.67 (d, 1H, J = 8), 5.40–5.90 (M, 2H), 4.51–4.83 (M, 1H), 1.28 (S, 3H), 1.18 (S, 3H) |
| 9-trans-α | 2,2-dimethyl-3-dichlorovinyl cyclopropyl acid chloride | α-1-hydroxy-dicyclopentadiene | 86% (m.p. 87–90°) | 5.80–6.20 (M, 4H), 5.63 (d, 1H, J = 8), 4.90–5.13 (M, 1H), 1.28 (S, 3H), 1.15 (S, 3H) |
| 10-α | α(p-chlorophenyl)-isovaleryl chloride | α-1-hydroxy-dicyclopentadiene | 64% | |
| 11-α | 2,2,3,3-tetramethyl cyclopropyl acid chloride | α-1-hydroxy-dicyclopentadiene | 50% | |
| 12-α | 2,2-dichloro-3,3-dimethyl cyclopropyl acid chloride | α-1-hydroxy-dicyclopentadiene | 33% | |
| 13-β trans- | 2,2-dimethyl-3-dichlorovinyl cyclopropyl acid chloride | β-1-hydroxy dicyclopentadiene | 96% | 5.40–6.20 (M, 6H), [1.20 (S), 1.18 (S) 3H], [1.33 (S), 1.30 (S) 3H] |
| 14 | 2,2-dimethyl-3-dichlorovinyl cyclopropyl | 1-adamantanol | 79% | |

TABLE I-continued

| Example | Acid Chloride | Alcohol | Yield | NMRδ (relative to TMS) |
|---------|---------------|---------|-------|------------------------|
|         | acid chloride |         |       |                        |

[a] J.O.C. 43, 147 (1978).
[b] Prepared from the corresponding aldehyde via di-isobutylaluminum hydride reduction.

The compounds of this invention have been found to exhibit considerable biological activity. They are especially potent pesticides when used to control or combat important agricultural pests. These compounds can be used in various ways to achieve biological action. They can be applied per se, as solids or in vaporized form, but are preferably applied as the toxic components in pesticidal compositions of the compound and a carrier. The compositions can be applied as dusts, as liquid sprays, or as gas-propelled sprays and can contain, in addition to a carrier, additives such as emulsifying agents, wetting agents, binding agents, gases compressed to the liquid state, odorants, stabilizers and the like. A wide variety of liquid and solid carriers can be used in the pesticidal compositions. Non-limiting examples of liquid carriers include water; organic solvents such as alcohols, ketones, amides, and esters; mineral oils such as kerosene, light oils, and medium oils, and vegetable oils such as cottonseed oil. Non-limiting examples of solid carriers include talc, bentonite, diatomaceous earth, pyrophyllite, fullers earth, gypsum, flours derived from cottonseeds and nut shells, and various natural and synthetic clays having a pH not exceeding about 9.5.

The amount of the compounds of this invention utilized in pesticidal compositions will vary rather widely. It depends to some extent upon the type of composition in which the material is being used, the nature of the condition to be controlled, and the method of application (i.e., spraying, dusting etc.). In the ultimate pesticidal composition, as applied in the field, pesticide concentrations as low as 0.001 weight percent of the total composition can be used. In general, compositions, as applied, containing about 0.05 weight percent pesticide in either liquid or solid carrier give excellent results. In some cases, however, stronger dosages up to about 10 weight percent may be required.

In practice, pesticidal compositions are usually prepared in the form of concentrates, which are diluted in the field to the concentration desired for application. For example, the concentrate can be a wettable powder containing large amounts of the compound of this invention, a carrier (e.g., attapulgite or other clay), and wetting and dispersing agents. Such powders can be diluted prior to application, by dispersing it in water to obtain a sprayable suspension containing the concentration of pesticide desired for application. Other concentrates can be solutions that can be later diluted, e.g. with kerosene. Thus, it is within the contemplation of this invention to provide pesticidal compositions containing up to about 80 percent, by weight of the composition, of a pesticidal compound of this invention. Accordingly, depending upon whether it is ready for application or it is in concentrated form, the contemplated pesticidal compositions contain between about 0.0001 percent and about 80 percent, by weight of the compositions, of a pesticidal compound of this invention and a carrier, liquid or solid, as defined hereinbefore.

INSECTICIDE TEST METHODS

Bait Test [Housefly (Adult)]
Method of Treatment

One milliliter of an aqueous solution or suspension of the candidate compound is pipetted into a 9 cm. petri dish containing filter paper and 0.1 gm. granular sugar. Ten adults are admitted and the dish is closed.

Method of Recording Results

Mortality is recorded after 24-75 hours. Compounds which produce 90% mortality are reevaluated at lower concentrations in secondary tests. Mode of action may be by stomach poison, contact or vapor.

Stomach Poison—Foliar Dip Test

Primary Screen
Souther Armyworm (Larva)
Mexican Bean Beetle (Larva)
Method of Treatment Lima bean leaves of a uniform size are momentarily dipped in a 500 ppm. water-acetone of the test material. Treated leaves are placed on moistened filter paper in 9 cm. petri dishes and allowed to air dry, and then are infested. The dishes are then closed.

Method of Recording Results

Mortality is recorded 72 hours after infestation. Compounds active at 500 ppm. are retested at 100 and 10 ppm.

All test results are recorded as percent mortality. In the tabulation of data, the insect species are abbreviated as follows: Housefly (HF), Mexican Bean Beetle (MB), and Southern Armyworm (SA).

The compounds of Examples 1 through 14 were subjected to the aforedescribed insecticide tests. Test concentrations and results are set forth in Table II together with structural formulae.

TABLE II

| Example | Rate (ppm) | % Control HF | MB | SA |
|---------|-----------|-----|-----|-----|
| 1-trans | 500 | 0 | 90 | 50 |
|         | 100 |   | 40 |    |
|         | 10  |   |    |    |
| 2       |     | 0 | 40 | 20 |
| 3       |     | 0 | 60 | 0  |
| 4       |     | 0 | 70 | 0  |
| 5       |     | 100 | 100 | 100 |
|         |     | 5 | 90 | 35 |
| 6-trans-endo |  | 100 | 100 | 10 |
|         |     | 25 | 85 |    |
|         |     | 15 | 0  |    |
| 6-trans-exo |   | 100 | 100 | 80 |
|         |     | 75 | 100 |    |
|         |     | 25 | 15 |    |
| 7-cis   |     | 0 | 90 | 0  |
| 8-trans |     | 100 | 100 | 100 |
|         |     |    | 80 | 25 |
| 9-trans-α | 500 | 100 | 100 | 100 |
|         | 100 | 85 | 100 |    |
| 10-α    |     | 10 | 0 | 0 |
| 11-α    |     | 0 | 50 | 0 |
| 12-α    |     | 0 | 20 | 0 |
| 13-trans-β |  | 0 | 60 | 0 |
| 14      |     | 100 | 100 | 100 |
|         |     | 70 | 100 | 100 |
|         |     | 5 | 40 | 0 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A compound having the formula: where $R^1$ is

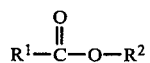

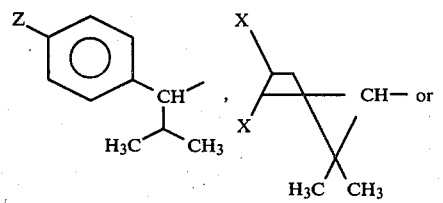

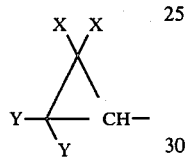

wherein X is F, Cl, Br or methyl; Y is methyl or Cl; Z is F, Cl, Br, $CF_3$, $CF_3O$, $CF_3S$, $CHF_2$, $CHF_2O$, or $CHF_2S$; and $R^2$ is

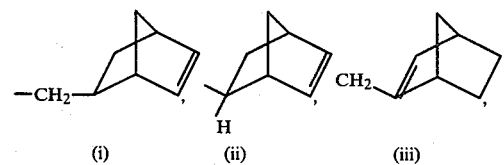

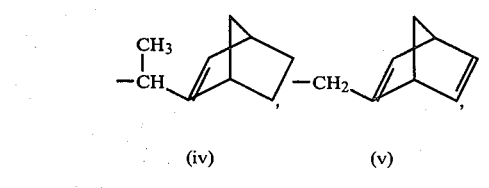

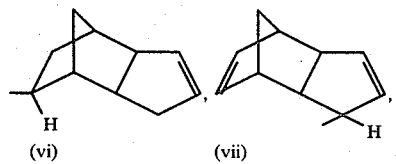

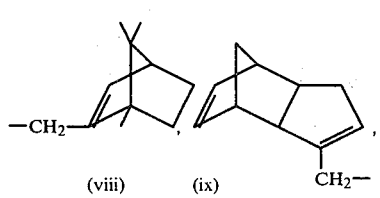

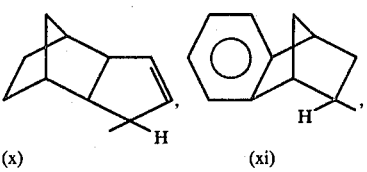

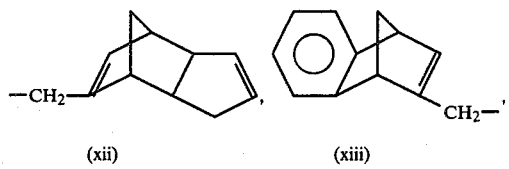

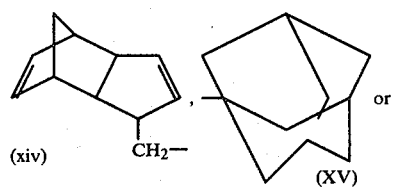

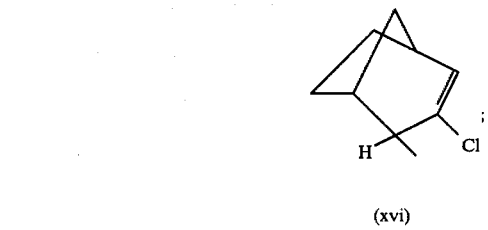

with the provisos that when $R^2$ is

then $R^1$ must be

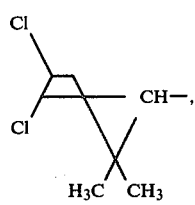

and when $R^2$ is

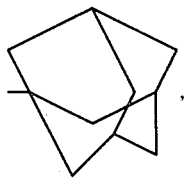

then $R^1$ must be

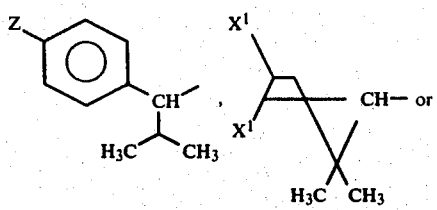

wherein $X^1$ is F, Cl or Br, and X, Y and Z are defined as above.

2. A compound of claim 1, wherein said compound has the formula:

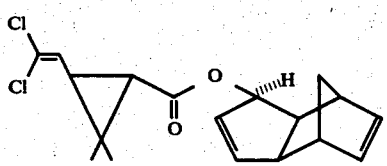

3. A compound of claim 1, wherein said compound has the formula:

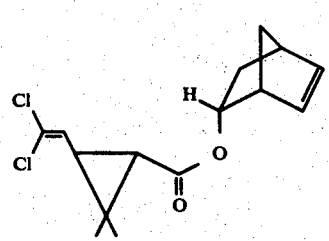

4. A compound of claim 1, wherein said compound has the formula:

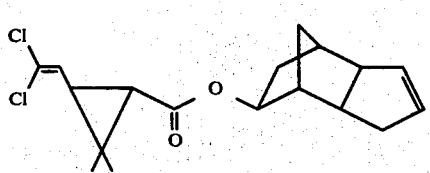

5. A compound of claim 1, wherein said compound has the formula:

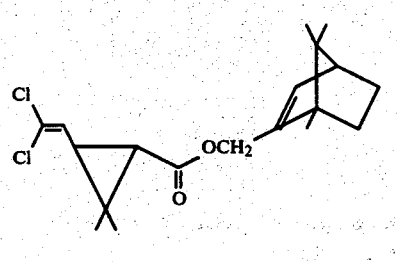

6. An insecticidal composition that comprises a carrier for an insecticide and an insecticidal amount of a compound of claim 1.

7. An insecticidal composition that comprises a carrier for an insecticide and an insecticidal amount of a compound of claim 2.

8. An insecticidal composition that comprises a carrier for an insecticide and an insecticidal amount of a compound of claim 3.

9. An insecticidal composition that comprises a carrier for an insecticide and an insecticidal amount of a compound of claim 4.

10. An insecticidal composition that comprises a carrier for an insecticide and an insecticidal amount of a compound of claim 5.

11. The method for combatting insects that comprises contacting them with an insecticidal amount of a compound of claim 1.

12. The method for combatting insects that that comprises contacting them with an insecticidal amount of a compound of claim 2.

13. The method for combatting insects that comprises contacting them with an insecticidal amount of a compound of claim 3.

14. The method for combatting insects that comprises contacting them with an insecticidal amount of a compound of claim 4.

15. The method for combatting insects that comprises contacting them with an insecticidal amount of a compound of claim 5.

16. A compound of claim 1, wherein $R^1$ is

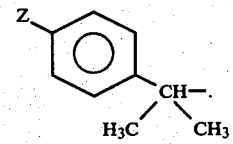

17. A compound of claim 1, wherein $R^1$ is

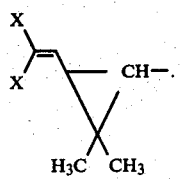

18. A compound of claim 17, wherein X is Cl.

19. A compound of claim 1, wherein $R^1$ is

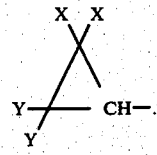

20. A compound of claim 1, wherein $R^2$ is

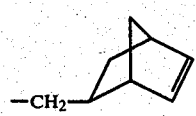

21. A compound of claim 1, wherein $R^2$ is

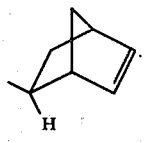

22. A compound of claim 1, wherein R² is

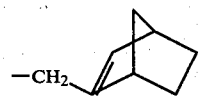

23. A compound of claim 1, wherein R² is

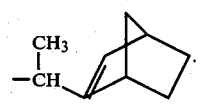

24. A compound of claim 1, wherein R² is

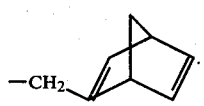

25. A compound of claim 1, wherein R² is

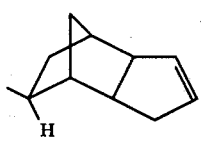

26. A compound of claim 1, wherein R² is

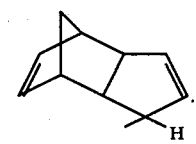

27. A compound of claim 1, wherein R² is

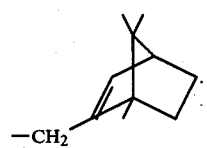

28. A compound of claim 1, wherein R² is

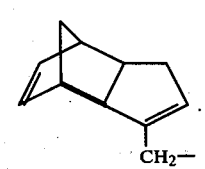

29. A compound of claim 1, wherein R² is

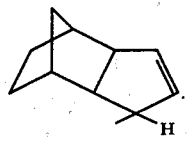

30. A compound of claim 1 wherein R² is

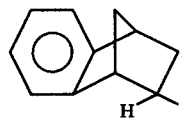

31. A compound of claim 1, wherein R² is

32. A compound of claim 1, wherein R² is

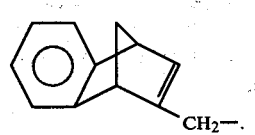

33. A compound of claim 1, wherein R² is

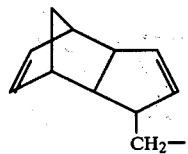

34. A compound of claim 1, wherein R² is

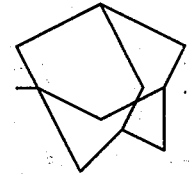

35. A compound of claim 1, wherein R² is

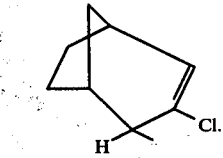

36. A compound of claim 1, wherein said compound has the formula:

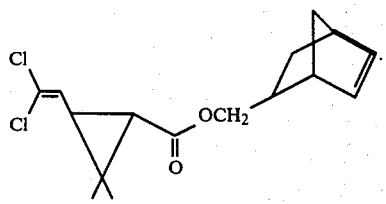

37. A compound of claim 1, wherein said compound has the formula:

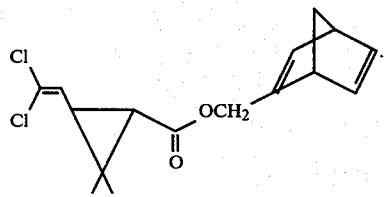

38. A compound of claim 1, wherein said compound has the formula:

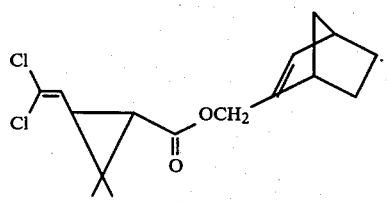

39. A compound of claim 1, wherein said compound has the formula:

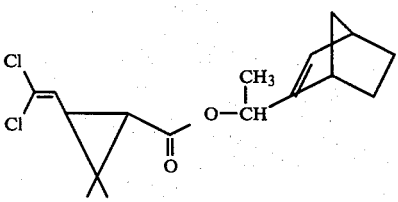

40. A compound of claim 1, wherein said compound has the formula:

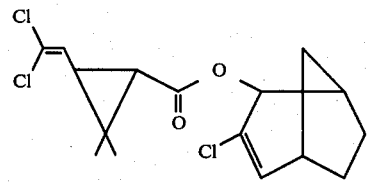

41. A compound of claim 1, wherein said compound has the formula:

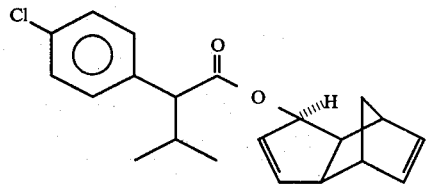

42. A compound of claim 1, wherein said compound has the formula:

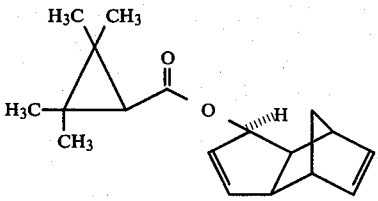

43. A compound of claim 1, wherein said compound has the formula:

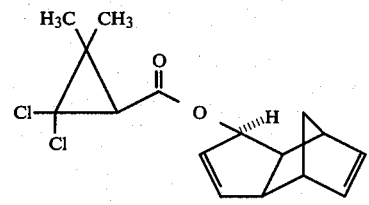

44. A compound of claim 1, wherein said compound has the formula:

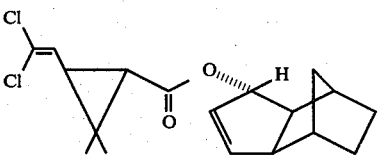

45. A compound of claim 1, wherein said compound has the formula:

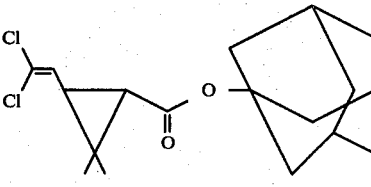

* * * * *